United States Patent [19]

Bogardus et al.

[11] Patent Number: 4,515,784
[45] Date of Patent: May 7, 1985

[54] REDUCING SEBUM SPREADING

[75] Inventors: Rodger E. Bogardus, Trumbull; Jon D. Packer, Stamford; James P. SaNogueira, Newtown, all of Conn.

[73] Assignee: Richardson-Vicks Inc., Wilton, Conn.

[21] Appl. No.: 552,473

[22] Filed: Nov. 16, 1983

[51] Int. Cl.$^3$ ............................................ A61K 31/695
[52] U.S. Cl. ........................................ 514/63; 514/859
[58] Field of Search ........................................... 424/184

[56] References Cited

U.S. PATENT DOCUMENTS

| | | | |
|---|---|---|---|
| 3,185,627 | 5/1965 | Kass | 424/184 |
| 3,860,712 | 1/1975 | Ferrari | 424/240 |
| 4,000,317 | 12/1976 | Menda et al. | 424/69 |
| 4,054,670 | 10/1977 | Buhler | 424/358 |
| 4,246,257 | 1/1981 | Elliott et al. | 424/78 |
| 4,335,104 | 6/1982 | Van Cleave | 424/59 |
| 4,370,319 | 1/1983 | Chapin et al. | 424/184 |

OTHER PUBLICATIONS

Dow Corning New Product Information Sheet—"Dow Corning ® X2-1146A Fluid".

*Primary Examiner*—Leonard Schenkman
*Attorney, Agent, or Firm*—Salvatore R. Conte

[57] ABSTRACT

A method and composition for treating human skin, having applicabiity to oily skin and acne in order to improve the condition thereof by reducing the spreadability of sebum on the skin surface, the invention involving the application to human skin so characterized of a composition comprising, as an active component to reduce the spreadability of sebum, an effective amount of a straight chain dimethyl silicone polymer having a molecular weight of about 50,000 or more and a viscosity of about 10,000 centistokes or more.

25 Claims, No Drawings

REDUCING SEBUM SPREADING

BACKGROUND OF THE INVENTION

Sebum, or skin oil, is produced in the sebaceous glands located in the pilosebaceous apparatus of the skin and reaches the skin surface through the duct of the hair follicles. The presence of excessive amounts of sebum on the skin surface often results in an unattractive cosmetic condition commonly known as "oily skin". Sebum also plays an important role in the pathogenesis of acne. Sebaceous gland activity is significantly increased in acne subjects and individuals with the most severe acne often have the highest sebum secretion rates.

The spreading of sebum on the skin surface is then an important cosmetic parameter since its distribution on the skin surface can determine the appearance of oiliness or greasiness and can contribute to the severity of acne.

It is advantageous, therefore, to have available means for reducing the flow of sebum over the surface of human skin, with particular regard to skin characterized by an excessive secretion or presence of sebum on the surface and to affect skin areas of acne patients.

It has now been discovered that straight chain dimethyl silicone polymers having a molecular weight of about 50,000 or more and a viscosity of about 10,000 centistokes or more may be employed to effectively so reduce the spreadability of sebum.

SUMMARY OF THE INVENTION

The present invention relates to a method and composition for the topical application of a straight chain dimethyl silicone polymer having a molecular weight of about 50,000 or more and a viscosity of about 10,000 centistokes or more for the treatment of human skin (including the scalp) by reducing the spreadability of sebum thereon. Such method provides for the physiologically effective treatment of human skin and has beneficial applications such as, for example, in cosmetics formulated for particular use on oily skin, such as, for example, pore cleansers, scalp and hair shampoos and conditioners, and the like following application of which the skin is perceived and felt to be less oily, and in the treatment of acne wherein the reduction of excessive spreading of sebum is particular desirable to help prevent spreading of the acne condition.

DETAILED DESCRIPTION OF THE INVENTION

The active compounds employed in this invention are straight chain dimethyl silicone polymers having the formula

$$(CH_3)_3Si \text{---} [OSi(CH_3)_2]_n \text{---} CH_3$$

wherein n is a positive integer sufficient to provide a polymer of molecular weight of 50,000 or more and having a viscosity of 10,000 centistokes or more. Preferably the polymer has a viscosity of more than 100,000 centistokes. A most preferred dimethyl silicone polymer is one having a molecular weight of about 330,000. Such high molecular weight dimethyl silicone polymers are available from Dow Corning Corporation of Midland, Mich. or General Electric Company of Fairfield, Conn. An especially preferred dimethyl silicone polymer is X2-1146A Fluid from Dow Corning Corporation and SE 30 Gum from General Electric Company.

It has now been found that the straight chain dimethyl silicone polymers of the foregoing formula markedly reduce the spreadability of sebum on human skin. The improvement provided by the present invention involves the use of this benefical effect in treating skin conditions characterized either (i) by excessive secretion or presence of sebum on the skin surface, e.g., oily skin, or (ii) by acne, and thereby improve the condition thereof by the topical application of appropriate compositions containing said dimethyl silicone polymers. Such topical compositions may be either cosmetic formulations for use on oily skin or therapeutically active anti-acne formulations.

The dimethyl silicone polymers of the aforesaid formula or a solubilized solution thereof may be incorporated into any suitable cosmetic or anti-acne pharmaceutically acceptable carriers. It has also been discovered that water may be present in the compositions and that the presence of water is not detrimental to the sebum-spreading reduction properties of the dimethyl silicone polymers of this invention. Most preferably, however, the compositions of the present invention are anhydrous.

The particular type of topical cosmetic composition, which may include, for example, hand, face and body lotions and creams, scalp and hair conditioners, lotions, gels and shampoos, just to name a few, is not critical. Such types of compositions are readily prepared by skilled cosmetic chemical formulators. Similarly, the particular type of anti-acne composition is not critical nor, for that matter, is the particular therapeutic anti-acne active ingredient, for example, benzoyl peroxide, sulfur, resorcinol, derivatives of retinoic acid, chlorhydroxyquinoline, hormonal and antibacterial agents, and the like. The aforementioned straight chain dimethyl silicone polymers are nontoxic to human skin, are compatible with hydrophilic adjuvants and can be readily incorporated into such topical compositions.

In preparing such compositions, it is quite apparent that the product should not be formulated in such manner or include any vehicle or ingredient which would substantially ineffectuate the activity of said dimethyl silicone polymers in reducing sebum spreadability on the skin surface when the product is topically applied. It is also evident that the product should be physiologically compatible with the skin and be cosmetically elegant.

For purposes of this invention, an effective amount of a dimethyl silicone polymer of the aforesaid formula is included as an active ingredient to reduce the spreadability of sebum on skin in the topical compositions for use herein and, generally, at least about 0.1 percent by weight, based on the weight of the total composition (i.e. "% w/w"), is found suitable. It has been found that reduction in sebum spreading on skin is obtained in topical compositions containing from about 0.1 to about 100% by weight of such dimethyl silicone polymers, more preferably from about 1 to about 90% by weight, most preferably about 3 to 15% by weight.

Depending upon the viscosity of the dimethyl silicone polymers of this invention they may be used per se or as solubilized solutions thereof in lower molecular weight dimethyl silicone polymers of molecular weight of less than about 50,000 and a viscosity of less than about 10,000 centistokes or in other solubilizing agents such as dimethyl silicone oligmers such as cyclodimethicone tetramer or cyclodimethicone pentamer or mixtures thereof. An especially preferred solubilizing agent is a mixture of cyclodimethicone tetramer and pentamer, especially a 90:10 w/w mixture of tetramer and pentamer. Said solubilizing agents can be employed as the carrier vehicle in the sebum spreading reducing compositions of this invention. An especially preferred composition for use in this invention comprises a 87.5% by weight of a polydimethylsiloxane of molecular weight of about 330,000 in 12.5% by weight of a 90:10 w/w mixture of cyclodimethicone tetramer and pentamer. Such a composition is available from Dow Corning Corporation of Midland, Mich. as DOW CORNING ® X2-1146A fluid.

The instant invention thus provides a method of treating human skin, characterized by an excessive secretion of sebum or by acne, to improve the condition thereof by reducing the spreadability of sebum on the skin surface which comprises topically applying to human skin so characterized a composition comprising, as an active component to reduce the spreadability of sebum, an effective amount of a dimethyl silicone polymer of this invention. The invention also provides novel anti-acne compositions for topical application comprising, as an active ingredient to reduce sebum spreading, an effective amount of said dimethyl silicone polymer.

The method of this invention, compositions for use therein and the reduction in sebum spreadability afforded by said dimethyl silicone polymers will be illustrated and better understood by reference to the following examples. The procedure utilized in testing for reduction in sebum spreadability is as follows.

Testing Protocol:

From 2 to 4 mg/cm$^2$ of the material to be tested is placed on the back of the hand and spread evenly covering a circular area of about 2 inches in diameter. After application of the testing material, a period of one hour is allowed at room temperature for equilibration. After this hour, a 4 μl drop, measured from a micropipette of artificial sebum supplemented with 13% by weight of squalane is deposited substantially in the center of the treated area. The formulation for artificial sebum is

| Ingredients | % w/w |
| --- | --- |
| Squalane | 18.0 |
| Corn Oil | 7.0 |
| 1:1 Mix of Glyceryl Dioleate:Oleic Acid | 1.0 |
| Oleic Acid | 27.0 |
| Ceraphyl 140 (Decyl Oleate) | 43.5 |
| Cholesterol Palmitate | 1.0 |
| Cholesterol | 2.5 |
|  | 100.0 |

After a spreading period of 10 minutes, a 1 cm diameter glass cylinder is placed over the cylinder and the sebum within the confines of the cylinder is extracted. The extraction is performed by pipetting 2×0.5 ml aliquots of hexane into the glass cylinder for 30 seconds without agitation. Both hexane extracts are each pipetted into a test tube and evaporated to dryness by a nitrogen gas evaporator. The residue is resolubilized with 0.2 ml hexane and 10 μl of tetracosane is added to the sample as an internal standard. The amount of sebum within the glass cylinder is precisely determined by gas-liquid chromatography (GLC) via determination of the amount of squalane contained in the extract. From this data, the area covered by the spreading of the artificial sebum is calculated. The greater the amount of squalane recovered from the extract, the greater the reduction in sebum spreading.

Various dimethyl silicone polymers compositions were tested according to the aforementioned testing protocol and the percent reduction in sebum spreading for such composition is recorded in the following Table.

TABLE

| | $(CH_3)_3Si\text{-}[OSi(CH_3)_2]_{\overline{n}}CH_3$ Polydimethylsiloxane | | |
| --- | --- | --- | --- |
| Example No. | Viscosity Centistokes | Average Molecular Weight | % Reduction In Sebum Spreading |
| 1 | 0.65* |  | 3 |
| 2 | 1.00* |  | 1 |
| 3 | 10.00* | 1,250 | −5 |
| 4 | 350* | 15,000 | 0 |
| 5 | 500* | 20,000 | −2 |
| 6 | 1,000* | 30,000 | 14.5 |
| 7 | 10,000* | 70,000 | 38 |
| 8 | 12,500* | 72,000 | 25 |
| 9 | 30,000* | 82,000 | 58 |
| 10 | 60,000* | 90,000 | 41.5 |
| 11 | 100,000* | 97,000 | 44 |
| 12 | 300,000* |  | 50 |
| 13 | 600,000* |  | 70 |
| 14 | (SE 30 Gum)* | 1–10,000,000 | 50 |
| 15 | (X2-1146A Fluid)** | 330,000 | 51 |
| 16 | SE 30 GumΔ |  | 40 |
| 17 | SE 30 GumΔΔ |  | 57.7 |
| 18 | SE 30 GumΔΔΔ |  | 64.6 |

*13% polydimethylsiloxane in a 90:10 w/w cyclodimethicone tetramer:pentamer.
**12.5% polydimethylsiloxane in a 90:10 w/w cyclodimethicone tetramer:pentamer.
Δ13% SE 30 Gum in Dow Corning DC 200 Fluid Dimethicone of viscosity of about 65 centistokes.
ΔΔ13% SE 30 Gum in Dow Corning Dimethicone Fluid of viscosity of about 500 centistokes.
ΔΔΔ13% SE 30 Gum Corning Dimethicone Fluid of viscosity of about 10,000 centistokes.

As seen from the data set forth in the preceding Table, the polydimethylsiloxanes having a viscosity of about 10,000 or more and a molecular weight of 50,000 or more provide significant sebum spreading reduction whereas the lower molecular weight/lower viscosity polydimethylsiloxanes do not provide significant sebum spreading reduction.

Moreover, the presence of water in such polydimethylsiloxane polymer composition was found not to be detrimental to the sebum spreading reduction properties thereof. When the silicone composition of Example 15 of the Table was mixed with 2%, 10% and 50% water and tested according to the aforesaid testing protocol the percent reduction in sebum spreading was 61%, 49% and 43%, respectively, for said aqueous compositions.

It will be understood by those having skill in the art that the invention is not limited to the specific examples which have been offered as particular embodiments and that modifications can be made without departing from the spirit thereof.

We claim:

1. A method of treating human skin, characterized by an exessive secretion of sebum or by acne, to improve the condition thereof by reducing the spreadability of sebum on the skin surface which comprises topically applying to human skin so characterized a composition for topical skin application comprising, as an active component to reduce sebum spreading, an effective amount of a dimethyl silicone polymer having the formula:

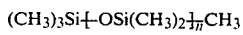

wherein n is a positive integer sufficient to provide a silicone polymer having a molecular weight of 50,000 or more and a viscosity of 10,000 centistokes or more.

2. The method of claim 1 wherein the polymer has a viscosity of more than 100,000 centistokes.

3. The method of claim 1 wherein the skin is characterized by an excessive secretion of sebum and the active component is in a non-toxic cosmetic carrier suitable for topical skin application.

4. The method of claim 1 wherein the skin is characterized by acne and the active component is in a topical anti-acne composition.

5. The method of claim 2 wherein the skin is characterized by an excessive secretion of sebum and the active component is in a non-toxic cosmetic carrier suitable for topical skin application.

6. The method of claim 2 wherein the skin is characterized by acne and the active component is in a topical anti-acne composition.

7. The method of claim 3 wherein the amount of dimethyl silicone polymer in said composition is in the range of from about 1 to about 90% by weight of the composition.

8. The method of claim 4 wherein the amount of dimethyl silicone polymer in said composition is in the range of from about 1 to about 90% by weight of the composition.

9. The method of claim 5 wherein the amount of dimethyl silicone polymer in said composition is in the range of from about 1 to about 90% by weight of the composition.

10. The method of claim 6 wherein the amount of dimethyl silicone polymer in said composition is in the range of from about 1 to about 90% by weight of the composition.

11. The method of claim 3 wherein the amount of dimethyl silicone polymer in said composition is in the range of from about 3 to about 15% by weight of the composition.

12. The method of claim 4 wherein the amount of dimethyl silicone polymer in said composition is in the range of from about 3 to about 15% by weight of the composition.

13. The method of claim 5 wherein the amount of dimethyl silicone polymer in said composition is in the range of from about 3 to about 15% by weight of the composition.

14. The method of claim 6 wherein the amount of dimethyl silicone polymer in said composition is in the range of from about 3 to about 15% by weight of the composition.

15. The method of claim 1 wherein the dimethyl silicone polymer is solubilized in a cyclodimethicone oligmer.

16. The method of claim 15 wherein the dimethyl silicone polymer is solubilized in a solubilizing agent which is a mixture of cyclodimethicone tetramer and pentamer.

17. The method of claim 16 wherein the solubilizing agent is a 90:10 w/w mixture of tetramer and pentamer.

18. The method of claim 17 wherein the dimethyl silicone polymer has a molecular weight of about 330,000 in a 12.5% by weight solution of the solubilizing agent.

19. The method of claim 2 wherein the dimethyl silicone polymer is solubilized in a cyclodimethicone oligmer.

20. The method of claim 19 wherein the dimethyl silicone polymer is solubilized in a solubilizing agent which is a mixture of cyclodimethicone tetramer and pentamer.

21. The method of claim 20 wherein the solubilizing agent is a 90:10 w/w mixture of tetramer and pentamer.

22. A topical anti-acne composition, containing a therapeutic anti-acne active ingredient the improvement characterized by the presence in said anti-acne composition of a sebum spreading reducing effective amount of a dimethyl silicone polymer of the formula:

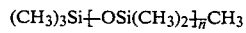

wherein n is a positive integer sufficient to provide a silicone polymer having a molecular weight of 50,000 or more and a viscosity of 10,000 centistokes or more.

23. The anti-acne composition of claim 22 wherein in the viscosity of the dimethyl silicone polymer is more than 100,000 centistokes.

24. The anti-acne composition of claim 23 wherein the dimethyl silicone polymer is present in the composition in an amount of from about 3% to about 15% by weight of the composition.

25. The anti-acne composition of claim 23 wherein the dimethyl silicone polymer is solubilized in a solubilizing agent which is a 90:10 w/w mixture of cyclodimethicone tetramer and pentamer and the dimethyl silicone polymer has a molecular weight of about 330,000 in a 12.5% by weight solution of the solubilizing agent.

* * * * *